(12) United States Patent
Bialecki et al.

(10) Patent No.: US 8,647,301 B2
(45) Date of Patent: Feb. 11, 2014

(54) SAFETY CATHETER DEVICE WITH REMOVABLY ATTACHED HOUSING

(75) Inventors: Dennis M. Bialecki, Oxford, CT (US); David J. Goral, Brookfield, CT (US); Alan D. King, Bradenton, FL (US)

(73) Assignee: Smiths Medical ASD, Inc., Rockland, MA (US)

( * ) Notice: Subject to any disclaimer, the term of this patent is extended or adjusted under 35 U.S.C. 154(b) by 0 days.

(21) Appl. No.: 13/527,248

(22) Filed: Jun. 19, 2012

(65) Prior Publication Data

US 2012/0259293 A1 Oct. 11, 2012

Related U.S. Application Data

(62) Division of application No. 11/161,541, filed on Aug. 8, 2005, now abandoned.

(51) Int. Cl.
*A61M 5/00* (2006.01)
*A61M 5/178* (2006.01)

(52) U.S. Cl.
USPC ..................... 604/110; 604/164.08

(58) Field of Classification Search
USPC ............. 604/197, 198, 110, 263, 162
See application file for complete search history.

(56) References Cited

U.S. PATENT DOCUMENTS

| | | | |
|---|---|---|---|
| 4,747,831 A | 5/1988 | Kulli | |
| 4,762,516 A | 8/1988 | Luther et al. | |
| 4,778,453 A | 10/1988 | Lopez | |
| 4,832,696 A | 5/1989 | Luther et al. | |
| 4,834,718 A | 5/1989 | McDonald | |
| 4,846,805 A | 7/1989 | Sitar | |
| 4,929,241 A | 5/1990 | Kulli | |
| 4,944,725 A * | 7/1990 | McDonald | 604/164.08 |
| 4,944,728 A | 7/1990 | Carrell et al. | |
| 4,950,252 A | 8/1990 | Luther et al. | |
| 4,952,207 A | 8/1990 | Lemieux | |
| 5,000,740 A | 3/1991 | Ducharme et al. | |
| 5,102,394 A | 4/1992 | Lasaitis et al. | |
| 5,108,379 A | 4/1992 | Dolgin et al. | |
| 5,135,504 A | 8/1992 | McLees | |
| 5,137,524 A | 8/1992 | Lynn et al. | |
| 5,156,599 A | 10/1992 | Ranford et al. | |
| 5,205,829 A | 4/1993 | Lituchy | |
| 5,215,525 A * | 6/1993 | Sturman | 604/164.08 |
| 5,215,528 A | 6/1993 | Purdy et al. | |

(Continued)

FOREIGN PATENT DOCUMENTS

| | | |
|---|---|---|
| CA | 2033361 A1 | 6/1992 |
| EP | 0750916 A2 | 1/1997 |

(Continued)

*Primary Examiner* — Kevin C Sirmons
*Assistant Examiner* — William Carpenter
(74) *Attorney, Agent, or Firm* — Wood, Herron & Evans, LLP

(57) ABSTRACT

A safety catheter device includes a catheter hub, a housing removably coupled to the catheter hub; a needle, and a member, the housing including a radially outwardly directed projection operable to engage the interior aspect of the catheter hub and radially moveable inwardly sufficiently to disengage therefrom, the projection being held against moving radially inwardly sufficiently to disengage when the needle is in a first position with the needle distal tip exposed and being free to move radially inwardly sufficiently to disengage coincident with the needle being moved into a second position with the needle distal tip disposed in the housing.

20 Claims, 9 Drawing Sheets

(56) References Cited

U.S. PATENT DOCUMENTS

| | | | |
|---|---|---|---|
| RE34,416 E | 10/1993 | Lemieux | |
| 5,300,045 A | 4/1994 | Plassche, Jr. | |
| 5,322,517 A | 6/1994 | Sircom et al. | |
| 5,328,482 A | 7/1994 | Sircom et al. | |
| 5,334,158 A | 8/1994 | McLees | |
| 5,344,408 A | 9/1994 | Partika | |
| 5,409,461 A | 4/1995 | Steinman | |
| 5,419,766 A | 5/1995 | Chang et al. | |
| 5,423,766 A | 6/1995 | Di Cesare | |
| 5,458,658 A | 10/1995 | Sircom | |
| 5,533,974 A | 7/1996 | Gaba | |
| 5,558,651 A | 9/1996 | Crawford et al. | |
| 5,584,810 A | 12/1996 | Brimhall | |
| 5,599,310 A * | 2/1997 | Bogert | 604/164.12 |
| 5,601,532 A | 2/1997 | Gaba | |
| 5,601,536 A | 2/1997 | Crawford et al. | |
| 5,611,781 A | 3/1997 | Sircom et al. | |
| 5,662,610 A | 9/1997 | Sircom | |
| 5,676,658 A | 10/1997 | Erskine | |
| 5,690,619 A | 11/1997 | Erskine | |
| 5,695,474 A | 12/1997 | Daugherty | |
| 5,697,907 A | 12/1997 | Gaba | |
| 5,738,660 A | 4/1998 | Luther | |
| 5,769,827 A | 6/1998 | DeMichele et al. | |
| 5,800,395 A | 9/1998 | Botich et al. | |
| 5,830,189 A | 11/1998 | Chang | |
| 5,879,337 A | 3/1999 | Kuracina et al. | |
| 5,911,705 A | 6/1999 | Howell | |
| 5,935,109 A | 8/1999 | Donnan | |
| 5,937,605 A | 8/1999 | Wendt | |
| 6,004,294 A | 12/1999 | Brimhall et al. | |
| 6,077,244 A | 6/2000 | Botich et al. | |
| 6,203,527 B1 | 3/2001 | Zadini et al. | |
| 6,213,978 B1 | 4/2001 | Voyten | |
| 6,221,047 B1 | 4/2001 | Greene et al. | |
| 6,280,419 B1 | 8/2001 | Vojtasek | |
| 6,298,623 B1 | 10/2001 | Wendt | |
| 6,322,537 B1 | 11/2001 | Chang | |
| 6,379,333 B1 | 4/2002 | Brimhall et al. | |
| 6,443,929 B1 | 9/2002 | Kuracina et al. | |
| 6,547,762 B1 | 4/2003 | Botich et al. | |
| 6,582,402 B1 | 6/2003 | Erskine | |
| 6,595,954 B1 | 7/2003 | Luther et al. | |
| 6,595,955 B2 | 7/2003 | Ferguson et al. | |
| 6,616,630 B1 | 9/2003 | Woehr et al. | |
| 6,623,458 B2 | 9/2003 | Woehr et al. | |
| 6,629,957 B1 | 10/2003 | Wiklund | |
| 6,629,959 B2 | 10/2003 | Kuracina et al. | |
| 6,652,486 B2 | 11/2003 | Bialecki et al. | |
| 6,652,490 B2 * | 11/2003 | Howell | 604/164.08 |
| 6,689,102 B2 | 2/2004 | Greene | |
| 6,695,814 B2 | 2/2004 | Greene et al. | |
| 6,732,991 B1 | 5/2004 | Zakrzewski et al. | |
| 6,749,588 B1 | 6/2004 | Howell et al. | |
| 6,796,962 B2 | 9/2004 | Ferguson et al. | |
| 6,860,871 B2 | 3/2005 | Kuracina et al. | |
| 6,902,546 B2 | 6/2005 | Ferguson | |
| 6,972,002 B2 | 12/2005 | Thorne | |
| 7,008,402 B2 | 3/2006 | Ferguson et al. | |
| 7,214,211 B2 | 5/2007 | Woehr et al. | |
| 7,238,169 B2 | 7/2007 | Takagi et al. | |
| 7,347,838 B2 | 3/2008 | Kulli | |
| 7,513,888 B2 | 4/2009 | Sircom et al. | |
| 7,534,227 B2 * | 5/2009 | Kulli | 604/164.08 |
| 7,597,681 B2 | 10/2009 | Sutton et al. | |
| 7,632,243 B2 | 12/2009 | Bialecki et al. | |
| 7,658,725 B2 | 2/2010 | Bialecki et al. | |
| 7,753,877 B2 | 7/2010 | Bialecki et al. | |
| 7,785,296 B2 * | 8/2010 | Muskatello et al. | 604/192 |
| 8,162,881 B2 | 4/2012 | Lilley, Jr. et al. | |
| 2002/0169418 A1 | 11/2002 | Menzi et al. | |
| 2002/0193745 A1 | 12/2002 | Ferguson | |
| 2003/0100868 A1 | 5/2003 | Ferguson et al. | |
| 2003/0199827 A1 | 10/2003 | Thorne | |
| 2004/0049155 A1 * | 3/2004 | Schramm | 604/110 |
| 2004/0078003 A1 | 4/2004 | Smith et al. | |
| 2004/0122373 A1 | 6/2004 | Botich et al. | |
| 2004/0127854 A1 | 7/2004 | Leinsing et al. | |
| 2004/0186434 A1 | 9/2004 | Harding et al. | |
| 2004/0204681 A1 | 10/2004 | Thoresen et al. | |
| 2004/0225260 A1 | 11/2004 | Villa et al. | |
| 2004/0236288 A1 | 11/2004 | Howell et al. | |
| 2004/0267204 A1 | 12/2004 | Brustowicz | |
| 2005/0038384 A1 | 2/2005 | Li | |
| 2005/0075609 A1 | 4/2005 | Latona | |
| 2005/0096592 A1 | 5/2005 | Carlyon et al. | |
| 2005/0113755 A1 | 5/2005 | Greene et al. | |
| 2005/0277879 A1 | 12/2005 | Daga | |
| 2007/0038184 A1 | 2/2007 | Bialecki et al. | |
| 2007/0038185 A1 | 2/2007 | Albert et al. | |
| 2007/0073221 A1 | 3/2007 | Bialecki et al. | |
| 2007/0179446 A1 | 8/2007 | Carrez et al. | |
| 2007/0191775 A1 | 8/2007 | Diep et al. | |
| 2007/0191776 A1 * | 8/2007 | Bialecki et al. | 604/164.08 |
| 2007/0191777 A1 | 8/2007 | King | |

FOREIGN PATENT DOCUMENTS

| | | |
|---|---|---|
| EP | 0832666 A2 | 4/1998 |
| EP | 1378263 A2 | 1/2004 |
| JP | 1995024071 | 1/1995 |
| JP | 2001190683 A | 7/2001 |
| JP | 2002210005 A | 7/2002 |
| JP | 2004-073403 A | 3/2004 |
| JP | 2004113394 A | 4/2004 |
| JP | 2004113523 A | 4/2004 |
| JP | 2004113524 A | 4/2004 |
| JP | 2004154364 A | 6/2004 |
| JP | 2004321489 A | 11/2004 |
| WO | 0006221 A1 | 2/2000 |
| WO | 2007018824 A2 | 2/2007 |

* cited by examiner

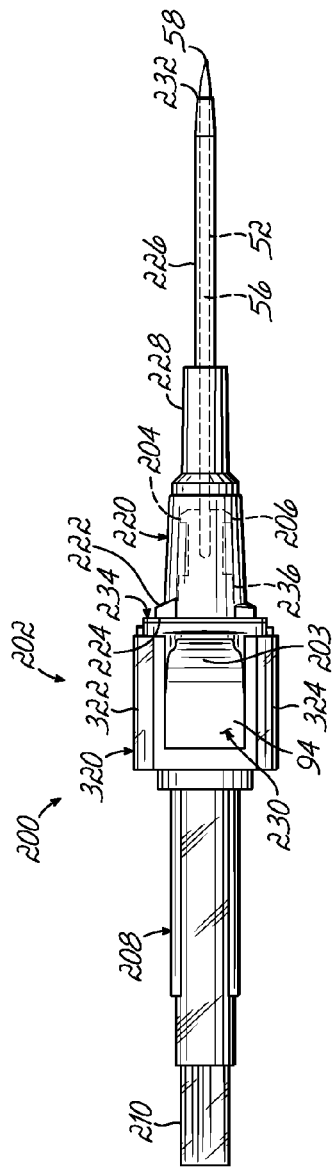
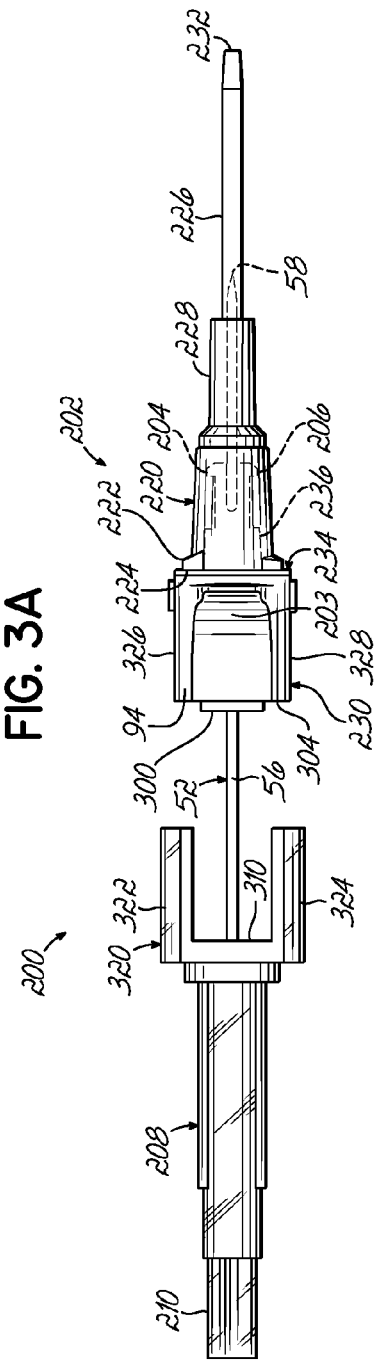
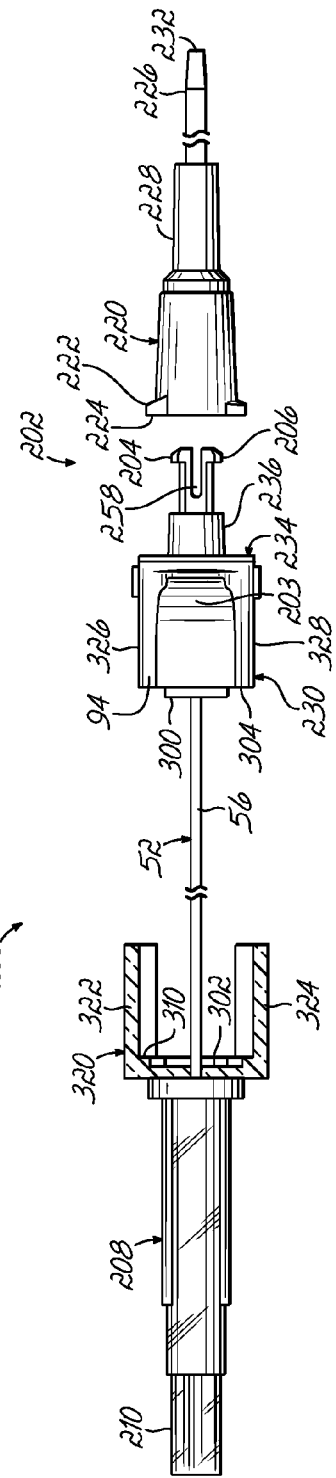
FIG. 3A
FIG. 3B
FIG. 3C

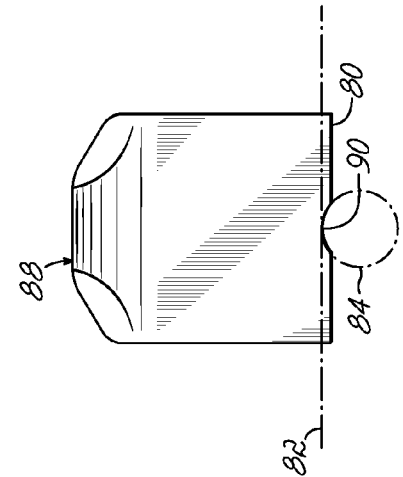
FIG. 4B
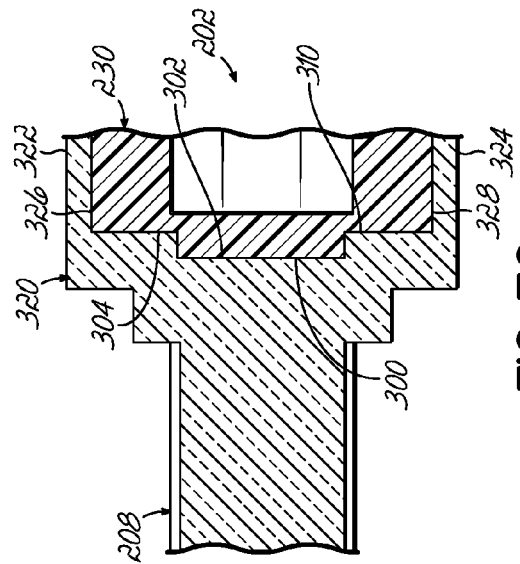
FIG. 7C
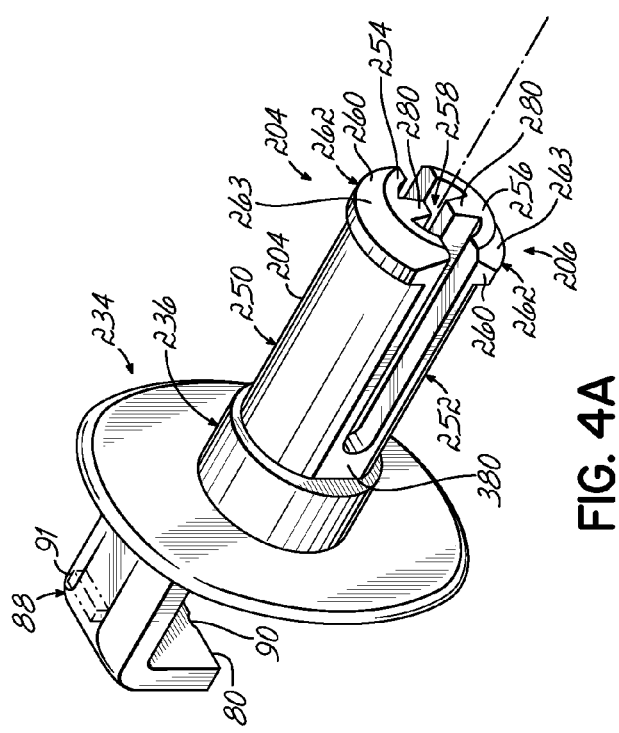
FIG. 4A
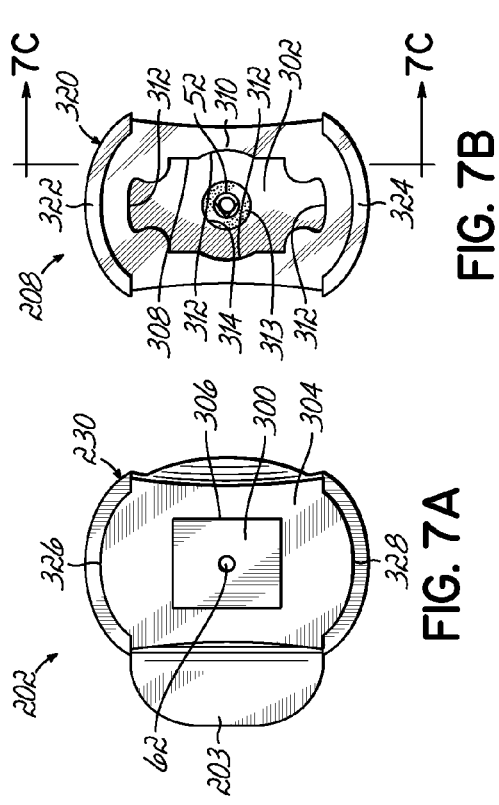
FIG. 7B
FIG. 7A

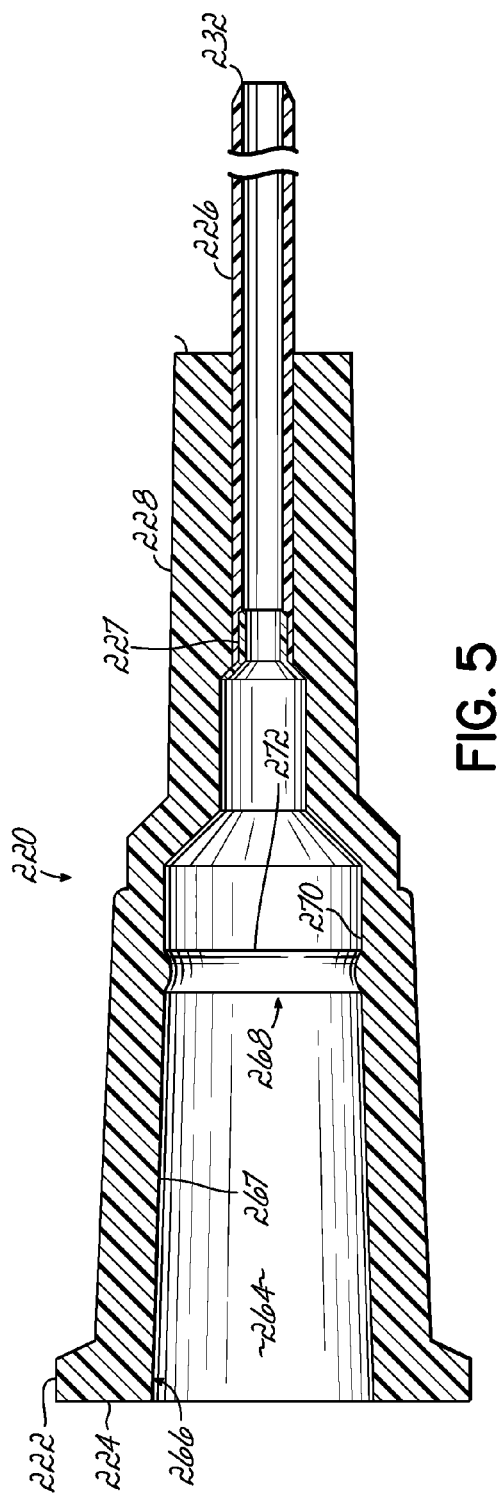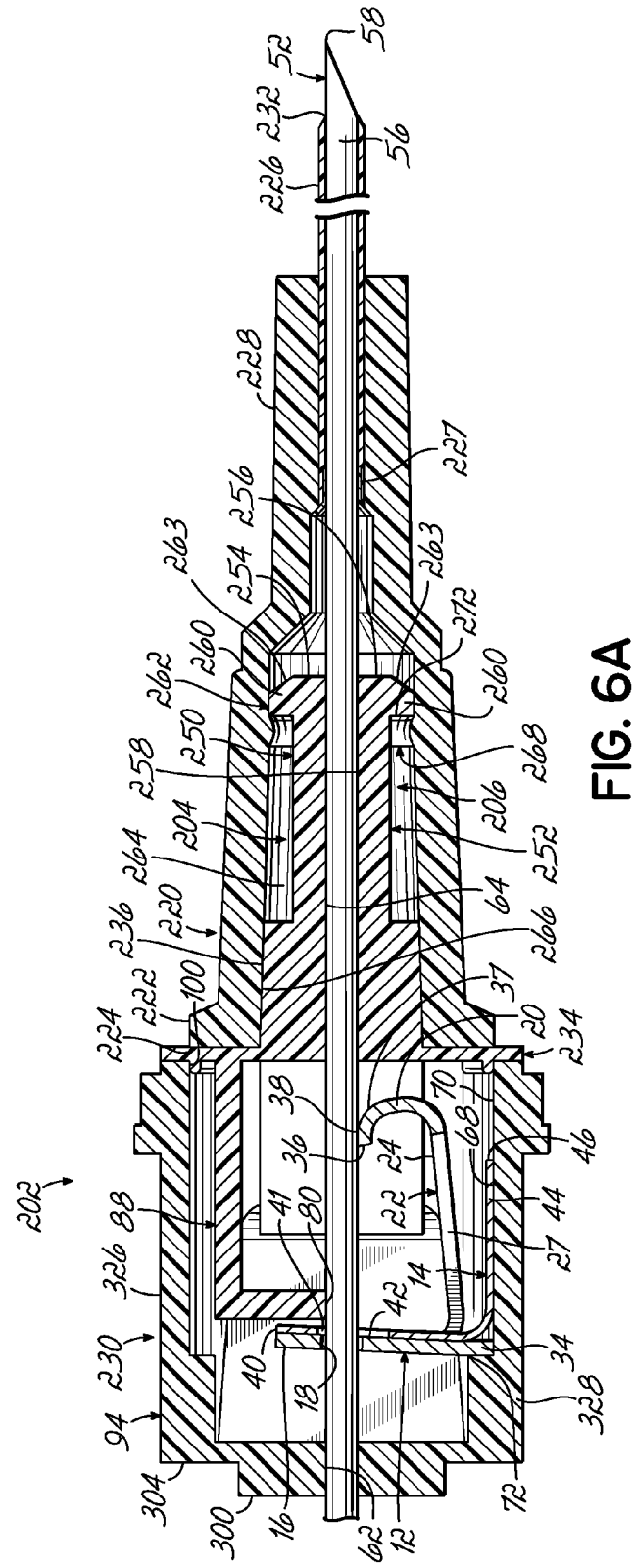

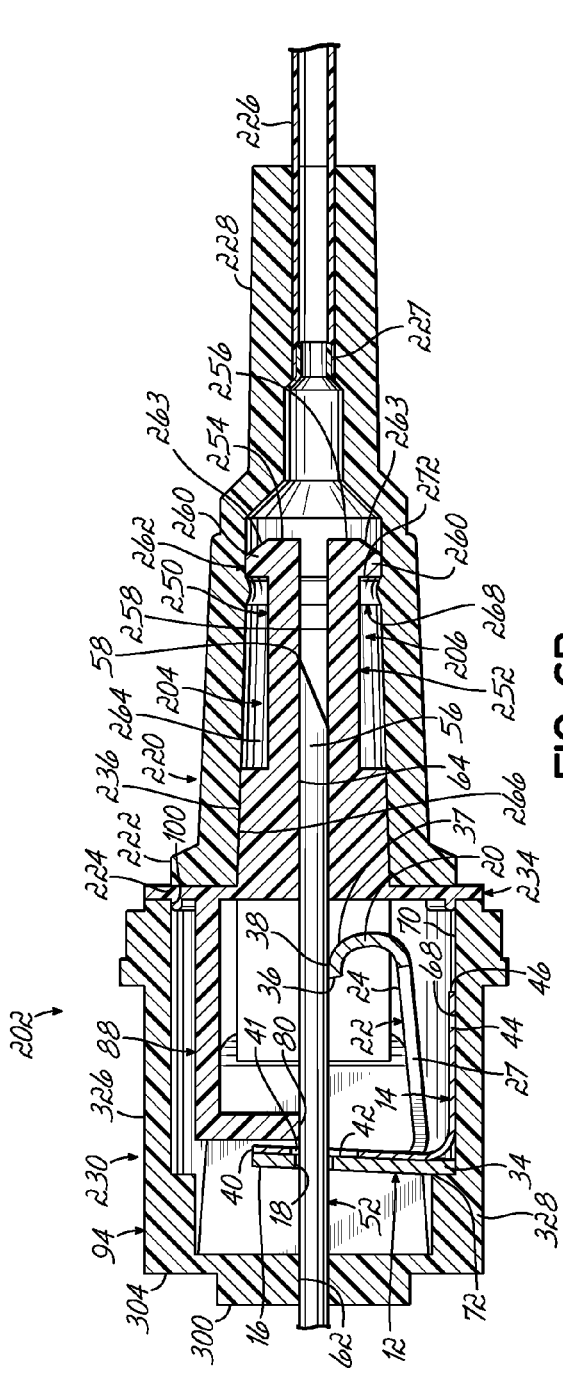
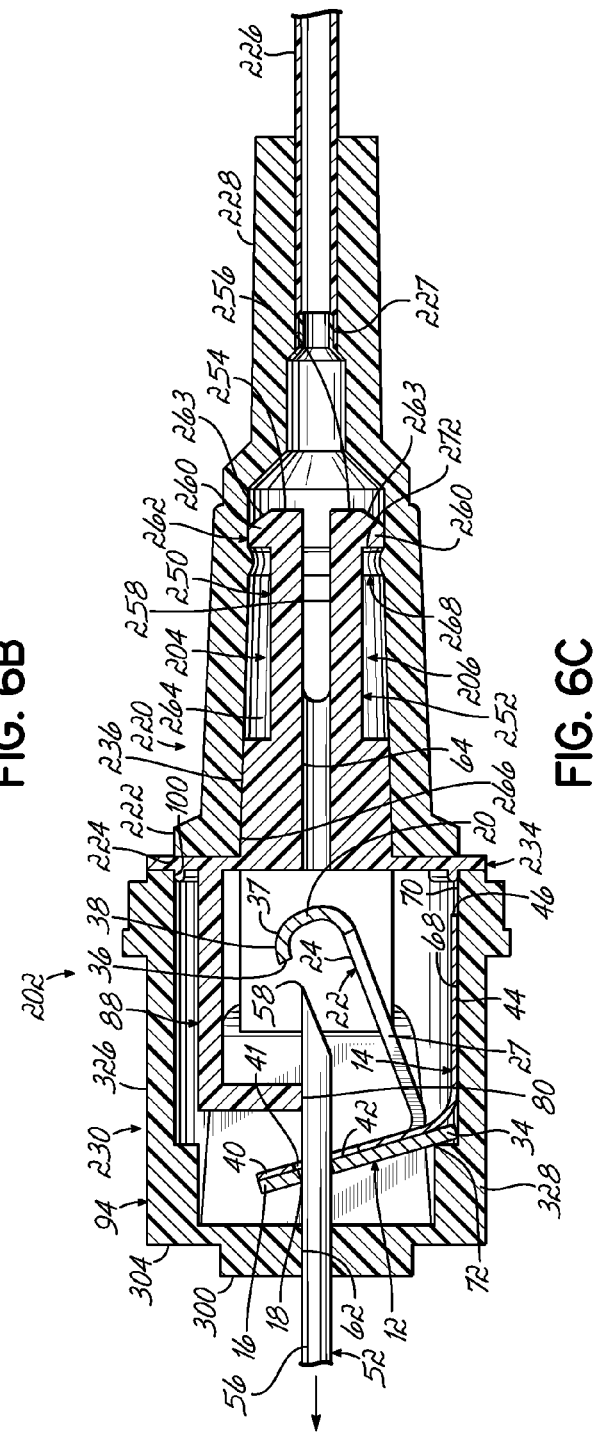
FIG. 6B
FIG. 6C

SAFETY CATHETER DEVICE WITH REMOVABLY ATTACHED HOUSING

RELATED CASES

This application is a divisional of U.S. patent application Ser. No. 11/161,541 filed Aug. 8, 2005, entitled Needle Guard Mechanism With Leaf Spring, the disclosure of which is incorporated herein by reference in its entirety.

FIELD OF THE INVENTION

The present invention relates to medical needles (such as hypodermic needles, catheter insertion needles or cannulae, or other sharp-tipped hollow or solid cannulae) and, more particularly, to needle guards to protect users and others from the sharp tip of the needle after withdrawal from a patient.

DESCRIPTION OF PRIOR ART

A variety of different needle guards have been developed or proposed to protect, i.e., to enclose or otherwise shield, sharp needle tips in recognition of the need to reduce or eliminate accidental needle-sticks. Some needle guards include a housing to enclose essentially the entire needle shaft and needle tip, such as the PROTECTIV Safety I.V. Catheter being marketed by Medex, Inc., the assignee hereof. Others include a clip that moves along the needle shaft to enclose the tip after use, such as shown in U.S. Pat. No. 6,652,486. Still other needle guards provide a housing that moves along the needle shaft with an enclosed active element to secure a distal portion of the needle with the tip inside the housing. Particularly advantageous forms of these needle guards include as the active element a canted-plate as described in U.S. Pat. No. 5,322,517.

In the canted-plate device of the '517 patent, a housing is provided through which the needle passes. Within the housing, a canting plate is defined by a wall with an aperture to slidably receive the needle shaft therethrough in a first state but which grips or bites into the needle shaft in a second, tilted or canted state relative to the first position. A second wall is connected to the first wall via an intermediate wall to define a generally rigid, single piece clip. The second wall includes a portion to ride along the needle shaft to hold the clip in the first state. When the needle tip is pulled into the housing and past the second wall portion, the clip can tilt into the second state such that the canting plate grips the needle shaft to prevent the needle from being pulled any further. Also, the second wall blocks the needle tip to prevent the needle from being pushed back out of the housing. A biasing spring is provided, bearing against the first wall, to urge the clip to the second state. The clip second and intermediate walls are to one side of the needle shaft in the first state with the spring to the other side of the needle shaft. While the clip design of the '517 patent has many advantages, further improvements and enhancements are desired.

One attempt to build upon the clip design of the '517 patent is shown in U.S. Pat. No. 6,280,419 which includes features intended to allow use of the clip with a guide wire. What is understood to be a commercial embodiment of the device of the '419 patent is the Arrow Radial Artery Catheterization device. The commercial embodiment is believed to have drawbacks including that its design also imposes significant drag force on the needle shaft, which make it difficult and undesirable to use.

Further, some needle guards are intended to be used with catheter assemblies. With such needle guards, it is advantageous to have a portion of the needle guard hold to the catheter hub while the needle projects out of the catheter tube, but to thereafter allow for ready removal of the needle guard upon withdrawal of the needle to the tip-protected position. One proposal is to provide a nose section of the needle guard with a pair of cooperating members extending from the needle guard housing. The cooperating members are sized to fit within the catheter hub and to normally define a passageway between the members, which is sized to slidably receive a needle shaft therethrough. One or both of the members has a detent at its distal end receivable in a respective radially outwardly extending recess formed in the interior wall of the catheter hub. The detent gives the member(s) the appearance of a duckbill. As will be appreciated, at least the distal portion of the catheter hub interior surface is tapered to female luer standards. The recess will be distal of the luer tapered surface and, when in the catheter hub, the detent(s) normally fit within the recess. When the needle shaft is removed from the passageway, one or both of the duckbill members is able to easily flex such that a slight tug on the housing causes the duckbill to yield against the recess allowing the needle guard to begin to come away from the catheter hub. But when the needle shaft is present, flexing of the members is limited such that the holding force is very high. The detents define an outer diameter of the duckbills sized to fit within the radially outwardly extending recesses. The inner diameter of the luer tapered surface, however, is smaller over a significant portion of its distal extent than the duckbill outer diameter. As a consequence, the duckbill members will remain flexed and will drag or scrape against the catheter hub interior surface during continued removal, which results in a feel and higher removal forces than might be desired by the medical practitioner.

The Arrow Radial Artery Catheterization device is an example of a duckbill design. But, the needle guard housing thereof cannot rotate relative to the catheter hub. Each duckbill detent has its own, limited circumferential length recess in the catheter hub, which thus holds the duckbill against rotation. It is often desirable to be able to rotate the needle guard housing relative to the catheter hub. As an example, it may be useful to rotate the components to thread the catheter tube into the patient. One proposed solution is to provide a continuous radially outwardly extending annular groove in the catheter hub such that the duckbill detent(s) may rotate therein as discussed in U.S. Pat. No. 6,221,047. But, in addition to the scraping problems mentioned above, a complete circumferential annular groove or recess in the catheter hub is believed to present manufacturing and product performance issues. Even one of the named inventors of the aforementioned '047 patent seemingly recognized the latter problem, and so subsequently proposed to go with the limited length recess such that the detent(s) would be inhibited from rotation within the catheter hub as discussed in U.S. Pat. No. 6,689, 102. There is thus still a need for a viable rotatable solution for the duckbill, as well as a need to reduce or eliminate the problem produced by the scraping of the detents with the inner surface of the catheter hub during removal.

SUMMARY OF THE INVENTION

In accordance with one of the principles of the present invention, there are provided canting-plate needle guards that have desired improvements and enhancements as compared to prior canted-plate designs. To that end, in one aspect, the needle guard includes a spring member, which may be a leaf spring, extending from the first wall past an edge of the intermediate wall, which may be defined by one or two struts, and into operative engagement with a bearing surface, with the extending portion of the spring member and the intermediate wall advantageously being to the same side of the needle. The bearing surface may be defined in or by a housing which contains the clip and spring member. The spring member and its operative relationship with the clip and/or the housing is believed to provide the appropriate biasing of the clip in a low profile and without imposing undue drag forces between the clip second wall portion and the needle shaft.

In a second aspect, the strut(s), i.e., the intermediate wall, advantageously extends from the first wall at an angle of less than 90 degrees relative to the first wall, and more advantageously, at an angle of between about 83 and about 87 degrees. That angling allows for an increase in the degree of clip rotation before gripping to the needle shaft to more reliably block or cap the needle tip. In a third aspect, a stylus is provided at the second wall to bear against the needle shaft thereby providing a smooth surface and reducing drag on the needle while also improving the tactile and audible feel and behavior of the needle guard. In a fourth aspect, the second wall may be generally L-shaped to define a lip at a free end which projects toward the first wall. The lip is disposed on one side of the needle shaft in the first state of the clip and assists in confining or capping the needle tip in the second state of the clip. The stylus may be a coined portion of the L-shaped wall.

In a fifth aspect, a heel extends from the first wall, with the heel and first wall disposed to opposite sides of the intermediate wall or strut. A ledge is provided with the heel abutting the ledge in the first state of the clip and pivoting about the ledge as the clip moves from the first state to the second state to thereby enhance its performance.

It will be appreciated that were the needle shaft to deflect in response to the force of the grip of the first wall, the shaft would seek to align with the aperture of the first wall, thus reducing the grip. To this end, in a sixth aspect, a needle support is fixedly positioned adjacent a plane transverse to a cylinder defined by the needle shaft so as to limit deflection of the needle shaft when the needle tip has been pulled into the needle guard. Thus, in the second state of the clip, the tendency of the needle shaft to flex is minimized by the needle support.

In addition to the foregoing aspects of the present invention, which can be used independently or in any desired combination, the present invention provides improvements to needle guards which can be used not only with canting-plate clips but with other needle guard designs as well. By way of example, needles or catheter assemblies with needles are usually provided with a protective sheath to enclose at least the needle tip and to overlie at least a portion of the needle guard prior to use. Gripping the needle hub to which the needle is affixed and the sheath portion overlying the needle guard to pull the sheath off could lead to inadvertent activation or removal of the needle guard from the catheter hub, thereby rendering the device unfit for use. One proposed solution is to provide a shroud on the needle hub that substantially encloses the needle guard when the needle hub is adjacent thereto. Thus, if the sheath portion overlying the needle guard is gripped, the force thereof will be transmitted to the shroud, rather than the needle guard, to reduce the likelihood of inadvertently activating the needle guard or pulling the needle guard loose from the catheter hub. That shroud, however, interferes with ready removal of the needle from the catheter in use. To that end, in accordance with another principle of the present invention, a split shroud is provided which overlies opposed portions of the needle guard but leaves another portion, such as finger tab thereof, exposed through the split shroud so as to allow for ready removal of the needle from the catheter in use.

In accordance with a yet further principle of the present invention, it is desired to hold the needle hub and needle guard from rotation before the needle guard is deployed so as to add stability when beginning a needle stick. To this end, cooperating structure, such as a lug with a non-circular periphery and a non-circular periphery recess, are provided on the respective confronting faces of the needle hub and needle guard. The cooperating structure engages when the needle hub is adjacent the needle guard, to thus hold them against relative rotation. As the components move apart, however, the cooperating structure no longer engages, thus allowing for such rotation.

In accordance with a still further principle of the present invention, and in particular for use with a catheter assembly, an improved needle guard duckbill catheter hub release mechanism is provided in which there is relative rotation between the needle guard and the catheter hub and without disadvantageous scraping during removal. To that end, an annular radially inwardly extending rib is provided in the catheter hub for selective engagement by the detent(s) of the extending cooperating members, rather than a radially outwardly extending recess or groove. The rib is distal of the luer tapered portion of the catheter hub interior surface, and the duckbill detents may be sized so as not to unduly scrape against the catheter hub interior on removal, yet to hold behind the rib prior to removal. The rib, which may be continuous or have gaps therein, presents advantages in manufacture and in performance of the device over the recesses or grooves characteristic of prior duckbill release mechanisms.

By virtue of the foregoing, individually and in various combinations, there are thus provided canting-plate needle guards that have improvements and enhancements as compared to prior canted-plate design. Also, by virtue of the foregoing, individually and in various combinations, there are thus also provided improvements to needle guards which can be used not only with canting-plate clips, but with other needle guard designs as well. These and other objects and advantages of the present invention shall be made apparent from the accompanying drawings and the description thereof.

BRIEF DESCRIPTION OF THE DRAWINGS

The accompanying drawings, which are incorporated in and constitute a part of this specification, illustrate embodiments of the invention, and together with the general description of the invention given above, and the detailed description of the embodiments given below, serve to explain the principles of the present invention.

FIGS. 2A' and 2B' are detail views of portions of FIGS. 2A and 2B, respectively for purposes of explaining certain principles of the present invention;

FIGS. 3A-3C are side views of a catheter assembly incorporating the various aspects of the present invention including a third embodiment of a needle guard for a needle of the catheter assembly;

FIG. 4A is perspective view of a nose portion of the needle guard housing of FIGS. 3A-3C for purposes of explaining certain additional principles and aspects of the present invention;

FIG. 4B is a rear view of the proximal aspect of the nose portion of FIG. 4A;

FIG. 5 is a cross-sectional view of the catheter hub of FIGS. 3A-3C for purposes of explaining the duckbill catheter hub release mechanism feature of the present invention;

FIGS. 6A-6D are cross-sectional views of the catheter assembly of FIGS. 3A-3C for purposes of illustrating operation of the duckbill catheter hub release mechanism of the second embodiment of the needle guard in accordance with certain principles of the present invention;

FIGS. 7A and 7B are end views of the confronting faces of the needle guard and the needle hub, respectively, of FIGS. 3A-3C, for purposes of illustrating an anti-rotation feature of the present invention;

FIG. 7C is a cross-sectional, partial view as taken along lines 7C-7C of FIG. 7B, showing the needle hub and needle guard housing of FIGS. 7A and 7B in engagement with one another for purposes of explaining the anti-rotation feature of the present invention;

DETAILED DESCRIPTION OF THE DRAWINGS

Figure 1:
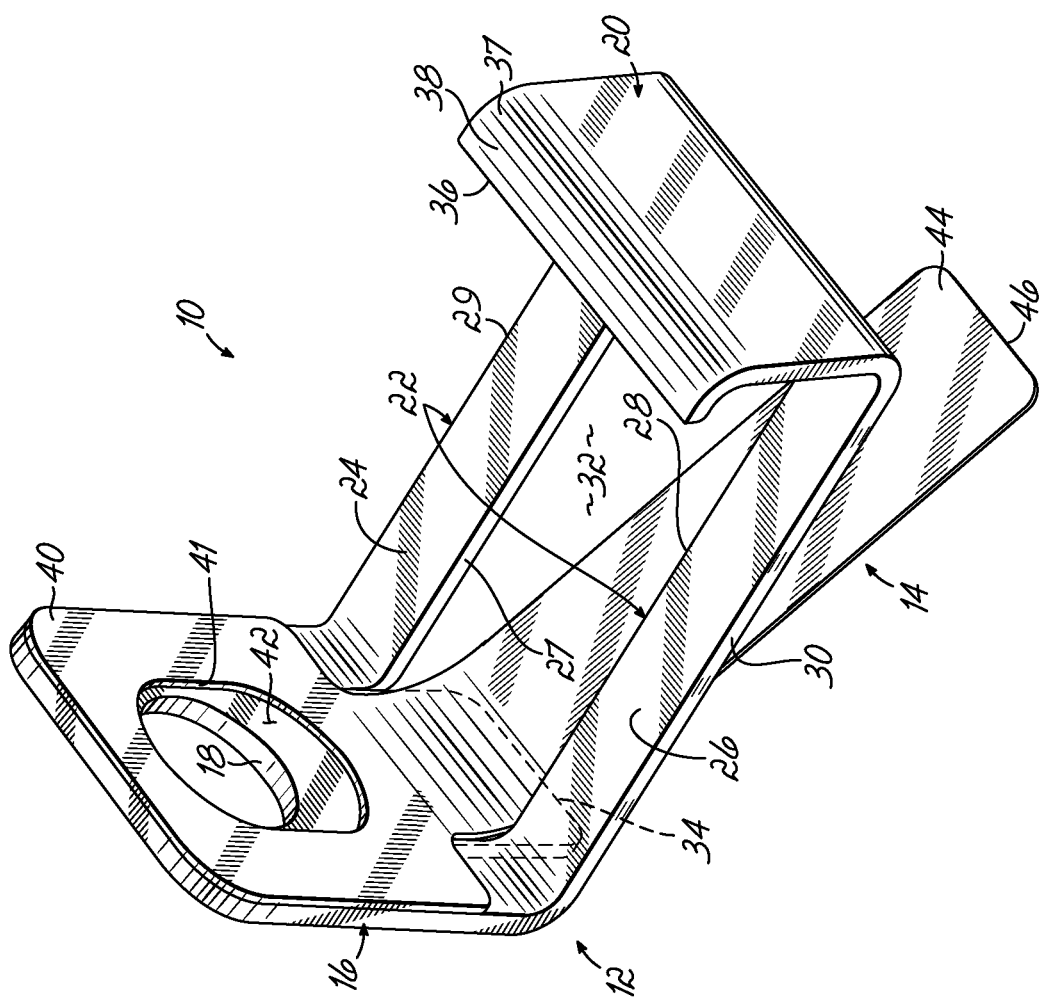
FIG. 1 is a perspective view of one embodiment of a needle guard defined by a canting plate clip with a leaf spring member in accordance with the principles of the present invention.

With reference to FIG. 1, there is shown one embodiment of a needle guard 10 including a canted-plate clip 12 and a spring member 14. Clip 12 includes a first wall 16 with an aperture 18, such as a circular hole, therethrough and a second wall 20 interconnected by an intermediate wall 22 shown herein as comprising first and second struts 24, 26, each having a respective inboard edge 27, 28 extending between walls 16 and 20 to define an aperture 32 therebetween, and outboard edges 29, 30. Extending from first wall 16 is a heel 34 (shown in dashed line in FIG. 1) such that first wall 16 and heel 34 are disposed to opposite sides of the struts 24, 26. Second wall 20 may have a lip portion 36 projecting generally toward first wall such that second wall 20 has a generally L-shape to it. The outer corner surface 37 of the L-shape second wall 20 may be coined so as to define thereat an arcuate stylus 38. Clip 12 is advantageously an integral component of rigid metal (an example of which is stainless steel) or plastic.

Although clip 12 is depicted in FIG. 1 as including two discreet struts 24, 26, those skilled in the art will recognize that alternative embodiments of the clip 12 may include only strut 24, or only strut 26, as the intermediate wall 22. Further, the strut 24 or 26 could be wider than depicted in the Figures, and could be so wide that they merge into, or it forms, a solid wall extending between the first and second walls 16, 20. In that case, an alternative spring member (not shown) extending past outer edge(s) 29 or 30 could be used.

Although spring member 14 could take any desired form of stored energy device, such as a coil or other wound spring, compressible foam substance or other material, or a compressible bladder, by ways of example, it will be described herein in the advantageous form of a leaf spring having a first end 40 with an opening 41 associated with an inner surface 42 of clip first wall 16 so as to overlie aperture 18 thereof, and having an elongated leaf 44 extending from the first wall 16 past the edges 27, 28 of struts 24, 26 through aperture 32 to a free end 46 of the leaf 44. Spring member 14 could be an integral part of clip 12, such that first end 40 is part of first wall 16 with leaf 44 extending therefrom. In that case, leaf 44 is advantageously thinner and more resilient than first wall 16 for purposes hereinafter to be described. Or, as shown in FIG. 1, spring member 14 is a separate, resilient component with first end 40 bearing against, and advantageously secured to, such as by welding or the like, inner surface 42.

Figure 2A:
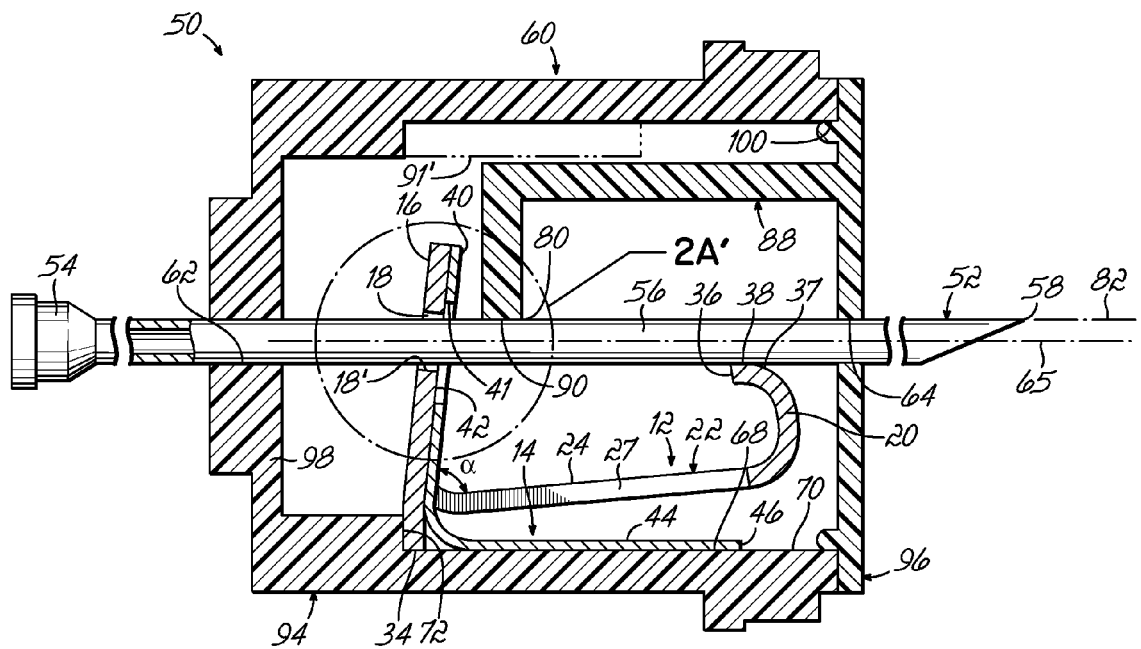
FIGS. 2A and 2B are cross-sectional views of a second embodiment of a needle guard having a housing and the clip of FIG. 1, showing the clip in first and second states with a sharp tip of a needle exposed and protected, respectively, for purposes of explaining certain principles of the present invention.
Figure 2A:
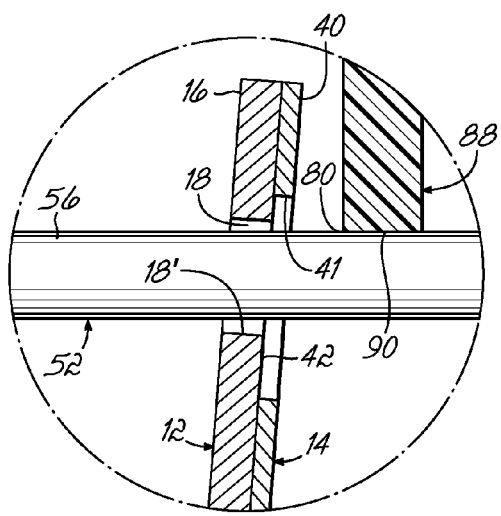
Figure 2B:
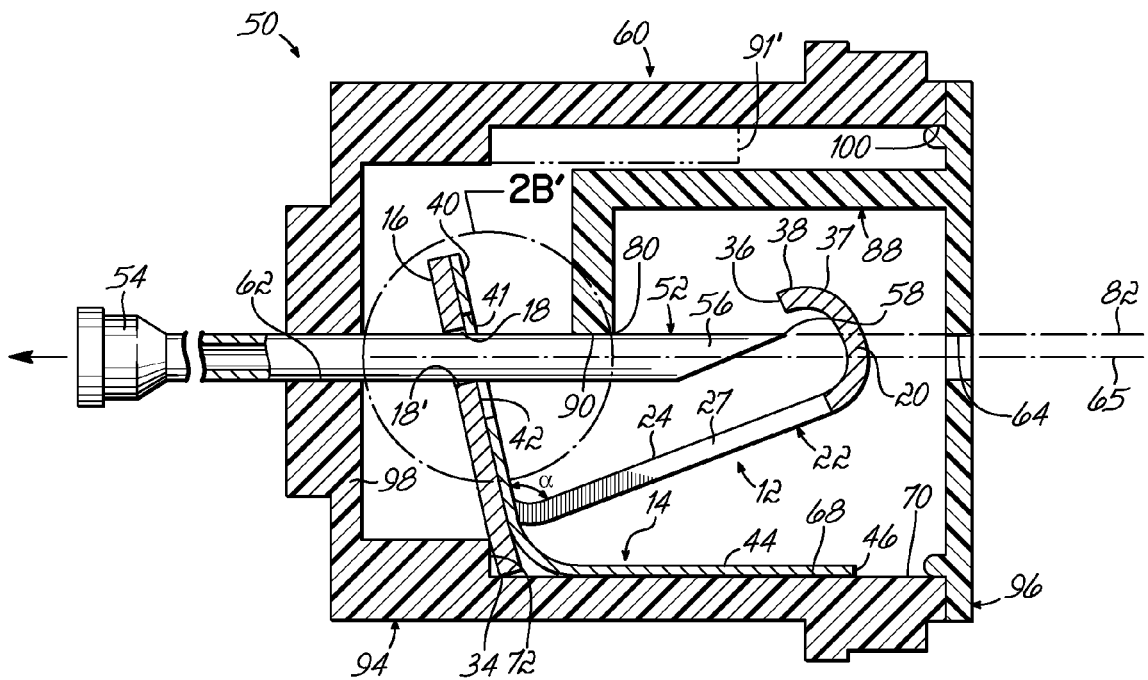
Figure 2B:
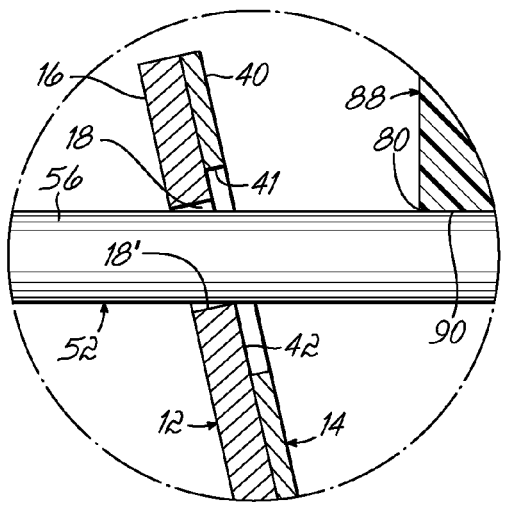

With reference to FIGS. 2A and 2B, there is shown a second embodiment of a needle guard 50 for a needle 52, such as a hollow hypodermic needle, a hollow or solid catheter insertion needle, or other similar sharp cannulae, attached to and extending from a needle hub 54, which in this embodiment is shown as adapted for a hypodermic needle thus defining a female luer lock attachment but could also or alternatively define a flash chamber. Needle 52 has a needle shaft 56 secured to and extending from needle hub 54 to a distal, sharp tip 58. While not required, the shaft 56 may be of a constant cross-sectional diameter. Needle guard 50 includes a housing 60 having a proximal opening 62 and a distal opening 64 sized to slidably receive the shaft 56 of needle cannula 52 through the housing such that in a first position of needle 52, sharp tip 58 may be distally exposed as shown in FIG. 2A, or in a second position of needle cannula 52, sharp tip 58 is pulled back (by either pulling needle shaft 56 proximally or pushing housing 60 distally, both referred to herein as proximal movement of needle cannula 52) into housing 60 as seen in FIG. 2B. Clip 12, wherein aperture 18 thereof is nominally sized relative to needle shaft 56 to selectively slidably receive or grip same, and spring member 14 of needle guard 10 of FIG. 1 are included as the active element to protect tip 58 within housing 60 as will now be described.

Clip 12 is situated within housing 60 such that aperture 18 is generally aligned along the longitudinal axis 65 of needle cannula 52, which axis is also defined between openings 62 and 64 of housing 60 and such that spring member 14 extends into operative engagement with a bearing surface 68 defined, for example, along an inner wall 70 of housing 60. Leaf 44 of spring member 14 and intermediate wall 22 are thus to the same side of needle shaft 56. Clip 12 has a first state, shown in FIG. 2A, in which first wall 16 is positioned generally vertically, although advantageously over-center distally, to allow needle shaft 56 to be slidably received through aperture 18 such that the inner periphery 18' of aperture 18 does not bite or grip into needle shaft 56 as seen in FIG. 2A'. In that first state of clip 12, second wall 20 has a portion, advantageously stylus 38 thereof, adapted to bear against shaft 56, and heel 34 is adjacent inner surface 70 and abutting ledge 72 of housing 60. When needle 52 is in the first position with tip 58 extending distally beyond clip 12, and particularly beyond opening 64 of housing 60, shaft 56 is in bearing relationship with stylus 38.

Spring member 14 biases clip 12 to cant first wall 16 proximally toward a second state shown in FIG. 2B with the needle 52 in the second position with sharp tip 58 of needle 56 within housing 60 such that tip 58 thereof is proximal of lip 36. Once tip 58 passes lip 36, heel 34 pivots about ledge 72 as first wall 16 cants to bring aperture periphery 18' into biting engagement with shaft 56 to thereby grip same, as seen in FIG. 2B', to resist further proximal movement of needle 52 relative to housing 60. Second wall 20, and especially lip 36 thereof, moves through and beyond axis 65 to go beyond tip 58 as seen in FIG. 2B, such that second wall 20 now confronts and thus blocks tip 58 from reemerging distally from housing 60. Lip 36 cooperates to confine tip 58 should it be able to move distally by some amount such that tip 58 is capped by clip 12 in the second state thereof.

As seen particularly in FIG. 2A, intermediate wall 22 is not at a right angle to first wall 16. Rather, intermediate wall 22 extends at an included angle a of less than 90 degrees, and advantageously between about 83 degrees and about 87 degrees, therefrom and towards needle shaft 56. The angling of the intermediate wall 22 allows first wall 16 to be slightly distally over-center or tilted (depending upon the gauge of needle 52) so that the degree of clip rotation to achieve the second state is increased as compared to a vertical wall 16 as in prior devices. The distal tilting is only a few degrees with hole 18 sized not to bite into needle shaft 56 when wall 16 is distally tilted. The increased degree of clip rotation helps assure that sharp tip 58 will be capped, even in the worst-case orientation of tip 58 as shown in FIG. 2B. Advantageously, needle 52 will be oriented 90° or 180° from that shown in FIG. 2B. Also, by making the included angle between walls 16 and 22 less than 90°, wall 22 typically angles towards needle shaft 56 such that the clip 12 is not as likely to bind against housing 60 even with larger gauge needles 52. Also, heel 34 may be at an angle of about 90 degrees to wall 22 such that heel 34 and wall 16 need not be coplanar.

In the second position of needle 52, with clip 12 in the second state, it will be appreciated that there is a flexing force on the distal tip end 58 of needle 52 which attempts to align that portion of needle shaft 56 with aperture 18. Were the shaft 56 to flex in that manner, there could be a reduction or loss of bite of periphery 18' on shaft 56, such that needle 52 might be able to be pulled proximally out of needle guard 50. To reduce that possibility, a needle support 80 is provided adjacent a plane 82 extending transverse, and possibly tangent, to the cylinder 84 defined by needle shaft 56 in the first position thereof (see FIG. 4B). Needle support 80 may be defined at the end of an integral projecting member 88 of housing 60, and advantageously may include a seat 90 (FIG. 4A) sized to slidably receive a portion of needle shaft 56 thereon. Seat 90 may be a slot or groove that complements the cylindrical shape of the outer surface of the needle shaft 56. In addition to the needle support 80, the needle 52 is also supported by the proximal opening 62 in the housing 60. These two points (needle support 80 and proximal opening 62) cooperate to hold needle 52 level and secure, and allow for the clip 12 to exert a gripping force on needle shaft 56 without adverse flexing thereof. A flex-limit stop in the form of a rib 91 (shown in dashed line in FIG. 4A as a lateral rib, but could be a longitudinal rib) may be included on the upper surface of projecting member 88 or, alternatively, a flex-limit stop rib 91' (shown in dashed line in FIGS. 2A and 2B) could be included as part of the housing interior surface 70 above member 88 to limit flexing (advantageously to 0.006") of member 88 such as from leveraging of needle shaft 56.

Housing 60 has a barrel or canister proximal portion 94 and a distal cap portion 96. Canister portion 94 includes inner wall 70 (and rib 91' if provided) and back wall 98 with opening 62 and a mouth 100 sized to matingly receive cap 96 thereto. Cap 96 includes opening 64, and is advantageously secured to mouth 100 of canister 94, such as by snap-fit, press-fit, and/or adhesive or ultrasonic welding. Canister 94 and cap 96 may have any desired cross-sectional shape, such as generally circular, such that housing 60 is generally cylindrical. Advantageously, the cross-sectional shape is rectangular by flattening opposed aspects thereof (as seen in FIG. 7A) so as to have a low profile allowing for a desirably shallow insertion angle. Housing 60 may also include finger ridges (not shown) for needle guard 50 to facilitate use by a medical practitioner (also not shown). Further, although distal end 58 of needle 52 is shown extending freely from needle guard 50, those skilled in the art will recognize that needle shaft 56 could also be received through a catheter assembly (such as assembly 200 of FIG. 3A). Further, while first wall 16 is shown as being rectangular, first wall 16 could be any other shape, such as square or disc-like, and aperture 18 could be other than a circular hole, provided tilting of first wall 16 into the second state of clip 12 results in gripping the needle shaft 56.

The foregoing construction and relationship of the components is believed to provide a needle guard that has very low drag forces, such that the tactile and audible sensations thereof are acceptable to the medical practitioner (not shown), while at the same time providing reliable protection of tip 58 thereby minimizing risk of accidental needle sticks therefrom.

In use, needle 52 is inserted into a patient (not shown) possibly with a syringe (not shown) attached to needle hub 54. After injecting medication, for example, while housing 60 is held steady, needle hub 54 and needle 52 are retracted to withdraw needle 52 from the patient and to withdraw needle tip 58 proximally into housing 60. Alternatively, needle 52 can be removed from the patient with housing 60 in place adjacent hub 54, and then housing 60 can be pushed down along shaft 52 to withdraw needle tip 58 proximally into housing 60. In either case, spring member 14 biases clip 12 toward the second state to protect the needle tip 58. Continued attempted proximal movement of the needle 52 results in increased binding force applied to needle shaft 56 thereby resisting such movement. Further, lip 36 of clip second wall 20 is now positioned to the other side of longitudinal axis 65 and beyond tip 58 of the needle 52. As a result, attempts to push the needle 52 distally will bring tip 58 underneath lip 36 and/or against second wall 20 to block the needle tip 58.

With reference to FIGS. 3A-3C, there is shown a catheter assembly 200 including a third embodiment of a needle guard 202 for protecting the tip 58 of needle 52. Needle guard 202 may be essentially the same as needle guard 50 of FIGS. 2A and 2B, except that it also includes a finger tab 203 and pair of duckbills 204, 206 (see FIG. 3C) as will be described. Further, needle 52 is a catheter insertion needle with a needle hub 208 shown as defining a flash chamber. Flash chamber 208 may include a vented port 210.

Catheter assembly 200 has a catheter hub 220 defining luer lugs 222 at its proximal end 224 and has a catheter tube 226 secured by eyelet 227 (FIG. 5) to, and extending distally from the distal end 228 of, catheter hub 220. Needle shaft 56 extends through housing 230 of needle guard 202 and through catheter hub 220 and catheter tube 226 with tip 58 exiting the distal end 232 thereof in a first position of needle 52 as seen in FIG. 3A. Housing 230 of needle guard 202 includes proximal canister 94, but has a modified cap 234, similar to cap 96 of FIG. 2A, but defining a nose portion 236 including the duckbills 204, 206. Needle support 208 is pulled proximally relative to needle guard 202 to begin to separate needle support 208 and housing 230 of needle guard 202 as seen in FIG. 3B. Continued proximal movement of needle 52 brings tip 58 into housing 230 to be protected in the secured position thereof (as described in connection with FIGS. 2B and 2B) and to also allow for release of housing 230 from catheter hub 220 as seen in FIG. 3C.

With further reference to FIG. 4A, extending distally from nose portion 236 of cap 234 of housing 230 are a pair of cooperating members 250, 252. Members 250, 252 extend to distal ends 254, 256 and define therebetween a passageway 258 nominally sized (also referred to herein as an inner diameter) to normally receive the shaft 56 of the needle 52 freely therethrough without changing the size of passageway 258 and thus without normally imposing significant drag forces on shaft 56. At least one, and advantageously both, of members 250, 252 may include a detent 260 at distal ends 254, 256 to thus define segments of an annular ring 262 and giving the cooperating members 250, 252 the shape of respective duckbills 204, 206. Detents 260 may be distally chamfered as at 263.

With reference to FIG. 5, it will be seen that catheter hub 220 includes an inner chamber 264 defined by interior surface 266 of catheter hub 220 having a proximal portion 267 tapered in accordance with ISO or other applicable standards for female luers. A generally annular rib 268 extends radially inwardly from interior surface 266 into chamber 264. Rib 268 is advantageously distal of luer tapered portion 267 so as not to interfere with male luer taper connections to catheter hub 220 Annular rib 268 and detents 260 cooperate to hold needle guard 202 to catheter hub 220 in the first position of needle cannula 52 (FIG. 3A) and to allow for release thereof by moving needle cannula 52 proximally towards the second position (FIG. 3C). In this regard, and with further reference to FIG. 6A, it will be seen that in the first position of needle cannula 52, shaft 56 thereof is in passageway 258 thus limiting the ability of either or both of cooperating members 250, 252 to compress (i.e., to flex radially inwardly). At the same time, detents 260 define an outer diameter of annular ring 262 that is slightly greater than the inner diameter of annular rib 268 and which may closely correspond to the inner diameter of catheter hub interior surface 266 just distal of annular rib 268 as at 270. Thus, with needle shaft 56 between cooperating members 250, 252 as seen in FIG. 6A, detents 260 provide a generally rigid hold to catheter hub 220 by cooperating with the distal-facing surface 272 of rib 268. Even as needle cannula progresses proximally to bring tip 58 towards housing 230, as seen in FIG. 6B, shaft 56 still provides a block to the radially inwardly flexing of members 250, 252.

Figure 6D:
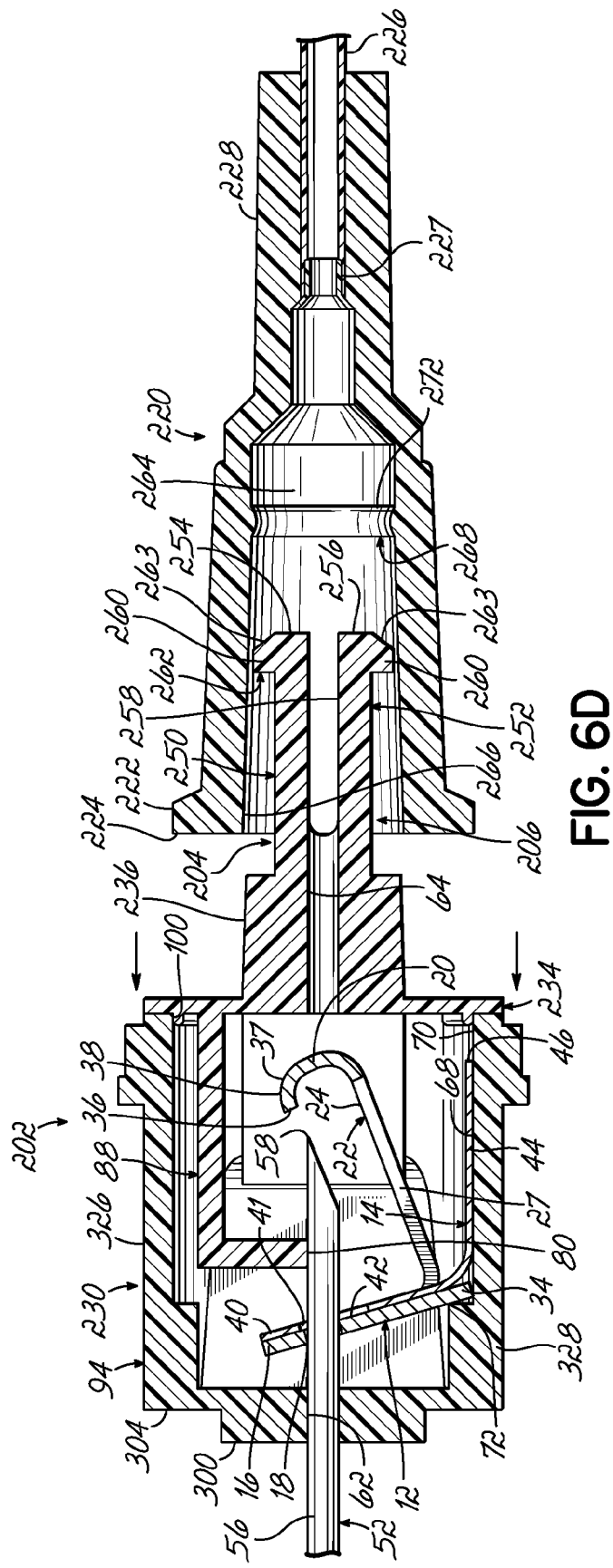

With the needle cannula 52 in the first position (FIG. 6A), detents 260 are seated past rib 268 in catheter hub 220 with a light frictional fit that desirably allows the healthcare user (not shown) to rotate catheter hub 220 relative to needle guard 202. It is not until needle shaft 56 is effectively proximally beyond passageway 258, such as with tip 58 protected by needle guard 202 in the second position of needle 52 as seen in FIG. 6C, that either or both of members 250, 252 are easily flexed. As a consequence, continued proximal pulling on needle guard 202 causes one or both of duckbills 204, 206 to easily flex enough that detents 260 overcome annular rib 268, and to then flex or uncompress back to the nominal position. As the interior surface 267 portion is tapered in accordance with luer standards, the minimum inner diameter thereof is generally not less than, and is advantageously larger than, the maximum outer diameter defined by detents 260, such that the detents generally will not adversely scrape on surface 266 proximal of rib 268 as the members 250, 252 are removed. Thus, needle guard 202 is allowed to easily come away from catheter hub 220, as seen in FIG. 6D, without any adverse feel or scraping and without any specific, difficult or strong tugging action of the user (not shown). Similarly, with needle shaft 52 out from within passageway 258, duckbills 204, 206 may be easily loaded into catheter hub 220 by pushing them into hub 220 (or pushing hub 220 over duckbills 204, 206) such that detents 260 impact against rib 268 to cause the cooperating members 250, 252 to flex slightly until detents 260 are distally beyond rib 258 at which time they flex back out to lightly hold to catheter hub 220. Needle shaft 52 may then be loaded to resist inward flexing of members 250, 252 greatly increasing the holding force. Alternatively, with shaft 52 in place, duckbills 204, 206 could be forced into hub 220. Chamfers 263 may help with loading duckbills 204, 206 into catheter hub 220.

Use of rib 268 overcomes drawbacks associated with prior recess-based duckbill release mechanisms. To that end, the rib is easier to manufacture and avoids requiring detents that are so large diametrically that they might drag or scrape on the interior surface of the catheter hub during removal.

The size of the passageway 258 may be closely dimensioned to the diameter of needle shaft 56 so the passageway 258 is largely taken up by the presence of needle shaft 56. Compression or other inward flexing of the cooperating members 250, 252 is thus limited, thereby restricting release of cooperating members 250, 252 from catheter hub 220. Tolerance of the gap between the relative inner diameter of passageway 258 of cooperating members 250, 252 and the outside diameter of needle shaft 56 may be selected to reduce the likelihood of removal of the duckbills 204, 206 from catheter hub 220 when needle 52 is present. These tolerances may vary for different gauge needles although clearances of between 0.0065" and 0.0135" are advantageous.

Members 250, 252 are shown defining a split cylinder. While they could be half-moon in cross-section, advantageously, each member 250, 252 is arcuate in cross-section and has an internal, depending longitudinal ridge 280 (FIG. 4A) to define, in effect, the inner diametrical size of the passageway 258. To that end, the radial depth of each ridge 280 may be selected based upon the gauge of needle 52, with the radial depth of ridge 280 being inversely related to the gauge of the needle 52 such that the radial depth is larger for small gauge needles and vice versa. Ridges 280 might be eliminated altogether for larger gauge needles 52. The arcuate shape and selective depth of ridges 280 to define the inner diameter of passageway 258 results in a generally consistent level of force between the duckbills 204, 206 and catheter hub 220 across a range of needle gauges, such that the medical practitioner (not shown) will have generally the same sense of feel and touch with the devices across a range of gauges. Cooperating members 250, 252 may be upper and lower segments of a split cylinder, or may define respective large and small aspects and/or side to side segments of a split cylinder. Moreover, while they are both described as being able to flex and with detents at their distal ends, it will be recognized by those of skill in the art that in only one of the members may be resilient enough to easily flex, only one member may include a detent, and/or the detent(s) may be away from the distal end(s). Also, while rib 268 is shown as being generally continuous, it may have one or more gaps (not shown). Advantageously, any such gap(s), if provided, would each be smaller than a circumferential width of the detent 260.

The needle guard duckbills 204, 206 and catheter hub rib 268 cooperate to define a duckbill release mechanism which, as are shown herein, may be combined with an active element to protect needle tip 58 in the form of a canting-plate clip. However, the duckbill release mechanism of the present invention is not limited in use to such active elements, but may be used with other clip designs and even non-clip-based needle guards such as those including housings that served as a needle guard. By way of example, the needle guard can be the needle guard housing of the PROTECTIV Safety I.V. Catheter being marked by Medex, Inc., the assignee hereof, and/or those shown in U.S. Pat. Nos. 4,762,516 and 4,747, 831, or the active element can include other structure to grip and/or block the needle as shown in U.S. Pat. Nos. 4,978,344; 5,215,528; 5,332,517; 5,328,482; and 5,558,651; European Patent No. 0,352,928 B2; U.S. Patent Publication No. 2006/0167405; and U.S. Pat. No. 7,347,838. Other features of the present invention are also not limited to needle guards based on canting-plate clips as will now be described.

Referring to FIGS. 7A-7C, in one aspect, the needle hub 208 and housing 230 include cooperating structure 300, 302 that hold them against relative rotation in the first position of the needle 52 to enhance stability when beginning a needle stick. More specifically, housing 230 includes at its proximal face 304 a projecting lug 300, having a non-circular peripheral edge 306. A recess or depression 302, also with a non-circular peripheral edge 308, is disposed in the distal face 310 of needle hub 208. As a consequence, when needle support 208 is adjacent housing 230 in the first position of needle 52, as seen in FIG. 7C, faces 304 and 310 are confronting with lug 300 engaging in recess 302 to hold the components against rotation. When needle 52 is moved out of the first position, lug 300 and recess 302 disengage thus allowing for relative rotation of hub 208 and needle guard 202. The peripheral edges 306, 308 of lug 300 and recess 302 are of complementary shape and advantageously define non-circular peripheries, such as a square, oval, or hexagon, for example. However, it will be understood that other complementary shapes may be used to prevent relative rotation between housing 230 and needle hub 208. Further the peripheral edge 308 of recess 302 may include one or more notch-outs as at 312. Needle 52 is secured to hub 208 such as by adhesive 313 in adhesive well 314 concentric with needle 52.

Figure 8:
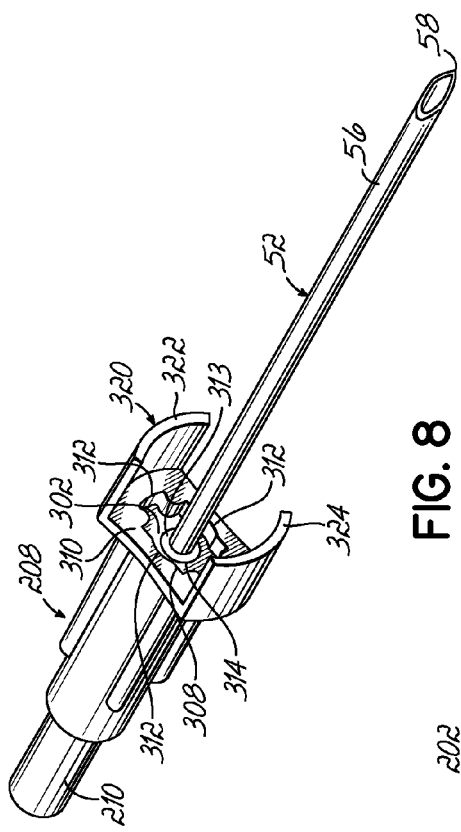
FIG. 8 is a perspective view of the needle hub and needle cannula of FIGS. 3A-3C illustrating a shroud at the distal end of the needle hub.
Figure 9:
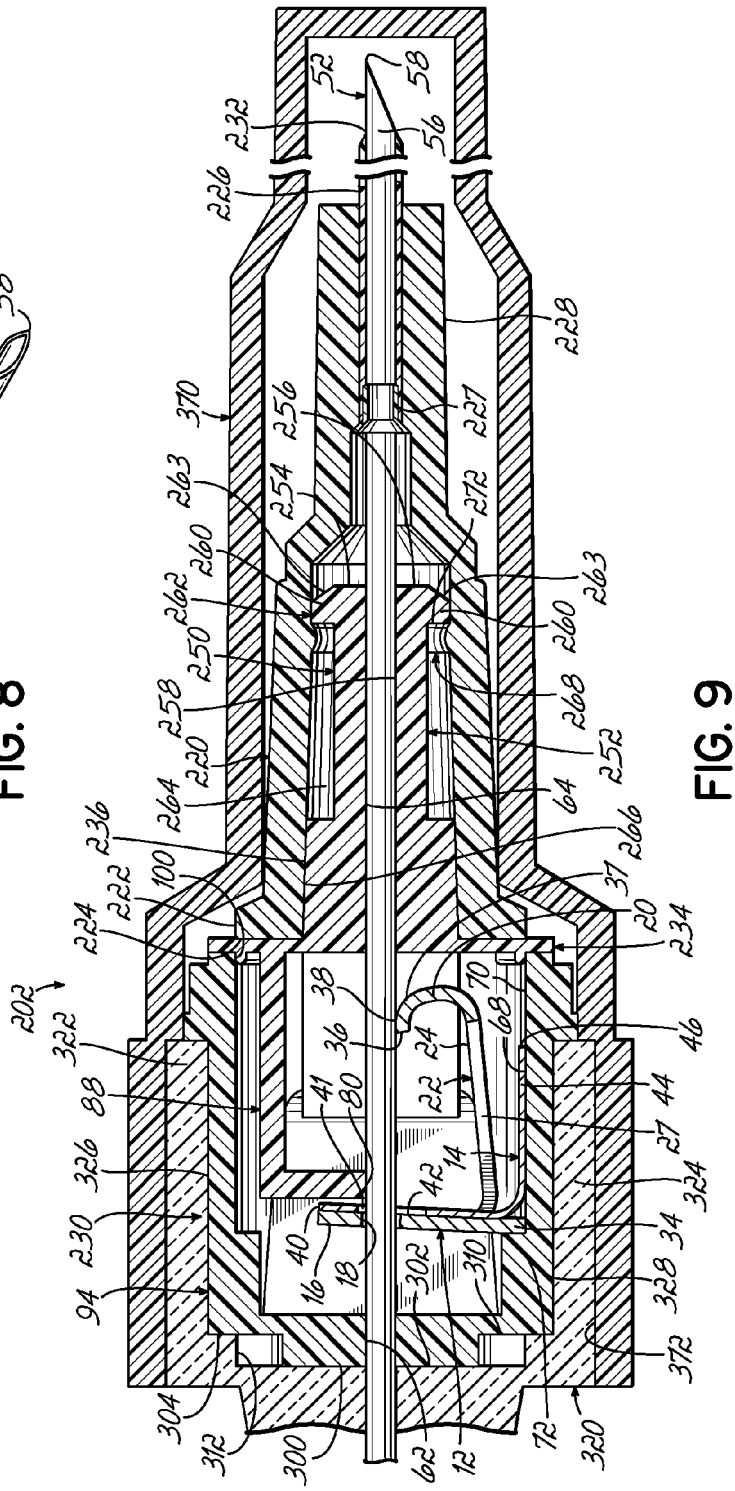
FIG. 9 is a cross-sectional, partial view of the catheter assembly of FIG. 3A with a protective sheath for purposes of explaining operation of the shroud in accordance with certain principles of the present invention.

Referring to FIGS. 8 and 9, in another aspect, needle hub 208 advantageously has associated with it a split shroud 320. Split shroud 320 has opposed arcuate legs 322, 324 extending from the distal end of hub 208. Legs 322, 324 are sized and positioned to overlie, and possibly conform to, opposed portions 326, 328 of needle guard 202 (and thus opposed arcuate portions of canister 94 of needle guard housing 230 and opposed portions of clip 12) in the first position of the needle 52 as seen in FIGS. 3A and 9, and to be spaced therefrom in the second position of the needle 52 as seen in FIG. 3C. Advantageously, legs 322, 324 are positioned such that a portion of the needle guard 220, such as finger tab 203, is exposed therebetween in the first position of needle cannula 52 as seen in FIG. 3A. In the first position of needle cannula 52, shown in FIG. 9, split shroud 320 overlies a portion of the needle guard 202, such as canister portion 94 of housing 230 and/or clip 12 leaving finger tab 203 exposed. The legs 322, 324 of split shroud 320 may be sized and positioned such that they engage housing 230 with a friction fit. Prior to use, a protective sheath 370 covers at least catheter tube 226 and possibly catheter hub 220, needle tip 58, and part or all of split shroud 320. Advantageously, split shroud 320 is disposed between the proximal mouth portion 372 of sheath 370 and needle guard 202. As a consequence, if an end user (not shown) grips the sheath portion 372, that force will be transmitted to split shroud 320, rather than directly to needle guard 202, to reduce the likelihood of inadvertently activating needle guard 202 or pulling needle guard 202 loose from catheter hub 220 before the device is ready for use. Mouth portion 372 may have a gap (not shown) to expose finger tab 203. However, in use, needle 52 may be readily removed such as by pushing on finger tab 203 exposed through split shroud 320.

In use of catheter assembly 200, sheath 370 is removed, and needle tip 58 inserted into a patient (not shown) to position catheter tube 226 as described, including if desired by rotation of catheter hub 220 relative to needle guard 202, but advantageously without relative rotation between needle hub 208 and needle guard 202. Once positioned as desired, needle hub 208 and needle 52 are moved proximally, such as with use of finger tab 203 (exposed through split shroud 320) as is well understood, to pull shaft 56 out of the catheter tube 226 and catheter hub 220, and toward a second position with tip 58 protected by needle guard 202. Needle guard 202 is similarly removed from catheter hub 220 leaving hub 220 ready for use. Advantageously, the drag forces on needle shaft 56 due to clip 12 are as low as possible. Moreover, the drag forces are advantageously lower than the forces required to separate the duckbills 204, 206 from catheter hub 202, whether or not shaft 56 is in passageway 258. Still further advantageously, the force required to separate the duckbills 204, 206 from catheter hub 220 with shaft 56 in passageway 258 (referred to as "catheter separation force") is greater than, and most advantageously is at least twice, the force necessary to let them come loose when the passageway 258 is not obstructed by needle shaft 56 such as in the second position of needle 52 (referred to as "catheter release force"). The catheter release force may be determined by the "duckbill free length," which is the length of the cooperating members 250, 252 from nose portion 236 (or any continuous portion as at 380). This length affects the stiffness of the cooperating members 250, 252, which in turn affects the catheter release force. For example, the longer the duckbill free length of a cooperating member 250 or 252, the less the stiffness leading to a more flexible member. Also, use of the arcuate shape to members 250, 252, and 260 and ridges 280 provide a generally consistent level of catheter release force (and/or catheter separation force) across a range of gauges of needle 52. That consistency is also enhanced by the lack of scraping between detents 260 and catheter hub surface 267. As can thus be seen, catheter assembly 200 provides a passive release of needle guard 202 from catheter hub 220. The normal activity of retracting needle hub 208 from catheter hub 220 activates needle guard 202 without any additional action by the healthcare worker (not shown). Similarly, further retraction of the needle hub 208, after activation, easily releases needle guard 202 from catheter hub 220 without additional manipulation by the healthcare worker.

By virtue of the foregoing, individually and in various combinations, there are thus provided canting-plate needle guards that have improvements and enhancements as compared to prior canted-plate design. Also, by virtue of the foregoing, individually and in various combinations, there are thus also provided improvements to needle guards which can be used not only with canting-plate clips, but with other needle guard designs as well.

While the present invention has been illustrated by the description of embodiments thereof, and while the embodiments have been described in considerable detail, it is not intended to restrict or in any way limit the scope of the appended claims to such detail. Additional advantages and modifications will readily appear to those skilled in the art. For example, while the Figures and the description herein show clip 12 as having a first wall 16 that cants proximally upon retraction of the needle 52, it will be understood by those of skill in the art that clip 12 could be designed such that wall 16 cants distally. Further, second wall 20 of clip 12 could include an opening (not shown) for a guide wire but not with clearance for needle 52 in the second sized state of clip 12. Further still, stylus 38 of second wall 20 could join directly to intermediate wall 22 of clip 12, such that the stylus defines the second wall. Further still, spring member 14 could extend past outboard edges 29, 30 of intermediate wall 22 rather than inboard edges 27, 28 of intermediate wall 22. Also, if clip 12 and spring member 14 are sized small enough, they could be fitted directly into a catheter hub with a bearing surface in the catheter hub. The invention in its broader aspects is, therefore, not limited to the specific details, representative apparatus and method, and illustrative examples shown and described. Accordingly, departures may be made from such details without departing from the spirit or scope of the general inventive concept.

What is claimed is:

1. A safety catheter device comprising;
   a catheter hub having a proximal end and a distal end and an interior aspect therebetween;
   a catheter tube extending from the distal end of the catheter hub;
   a needle having a shaft terminating in a distal sharp tip;
   a housing having a proximal end and a distal end, the housing being removably coupled to the catheter hub; and
   a member having a proximal end with an aperture and a distal end, the member being disposed distal of the housing proximal end and proximal of the catheter tube, the housing and the member adapted to slidably receive the needle therethrough between (a) a first position with the needle shaft extending through the aperture of the member and distally of the member distal end through the catheter tube with the needle distal tip exposed out therefrom and the member distal end bearing against the needle shaft, and (b) a second position with the needle shaft removed from the catheter tube, the needle distal tip disposed within the housing proximal of the housing distal end and proximal of the member distal end, and with the needle shaft extending through the aperture of the member, the member distal end being proximal of the housing distal end with the needle in the second position and being operable to maintain the needle distal tip within the housing after the needle has moved from the first position to the second position;
   the housing including a radially outwardly directed projection and a support being positioned radially inwardly of the projection and extending proximally thereof, the projection being operable to engage the interior aspect of the catheter hub and radially moveable inwardly sufficiently to disengage therefrom, the projection being held against moving radially inwardly sufficiently to disengage when the needle is in the first position and being free to move radially inwardly sufficiently to disengage coincident with the needle being moved into the second position,
   the housing defining a passageway portion starting at a distal-most end of the housing and extending proximally along the support, the passageway portion being distal of the needle in the second position, no part of the housing defining the passageway portion being in direct contact with the needle in the first position.

2. The safety catheter of claim 1, the member distal end being proximal of the housing distal end and the projection with the needle in the second position.

3. The safety catheter of claim 1, the radially outwardly projection being deflectable against the interior aspect of the catheter hub so as to come away therefrom.

4. The safety catheter of claim 1, the distal end of the member bearing against the shaft of the needle with the needle in the first position.

5. The safety catheter of claim 1, the distal end of the member including a wall with an aspect thereof bearing against the shaft of the needle with the needle in the first position.

6. The safety catheter of claim 5, the wall blocking the tip of the needle in the second position of the needle.

7. The safety catheter of claim 1, the distal end of the member including a wall, the wall blocking the tip of the needle in the second position of the needle.

8. The safety catheter of claim 1, in the first position of the needle the distal end of the housing situated inside the catheter hub and the proximal end of the housing situated outside of the catheter hub.

9. The safety catheter of claim 8, the housing including a distally projecting arm supporting the radially outwardly projection, the distally projecting arm extending distally into the catheter through the proximal end thereof 10. The safety catheter of claim 1, the housing including a distally projecting arm supporting the radially outwardly projection, the distally projecting arm extending distally into the catheter through the proximal end thereof 11. The safety catheter of claim 1, the member being disposed in the housing.

12. The safety catheter of claim 11, the member being an active element.

13. The safety catheter of claim 12, the active element being a clip.

14. The safety catheter of claim 12, the active element having a portion biased against the shaft of the needle with the needle in the first position.

15. The safety catheter of claim 14, the active element portion blocking the tip of the needle in the second position of the needle.

16. The safety catheter of claim 1, the housing and the member being separate components.

17. The safety catheter of claim 16, the member being contained within the housing.

18. The safety catheter of claim 1, the member distal end being proximal of the housing distal end with the needle in the first position.

19. A safety catheter device comprising;
   a catheter hub having a proximal end and a distal end and an interior aspect therebetween;
   a catheter tube extending from the distal end of the catheter hub;
   a needle having a shaft terminating in a distal sharp tip;
   a housing having a proximal end and a distal end, the housing being removably coupled to the catheter hub; and
   a member having a proximal end with an aperture and a distal end, the member proximal end being separate and movable relative to the housing proximal end, the member being disposed proximal of the catheter tube, the housing and the member adapted to slidably receive the needle therethrough between (a) a first position with the needle shaft extending through the aperture of the member and distally of the member distal end through the catheter tube with the needle distal tip exposed out therefrom and the member distal end bearing against the needle shaft, and (b) a second position with the needle shaft removed from the catheter tube, the needle distal tip disposed within the housing proximal of the housing distal end and proximal of the member distal end, and with the needle shaft extending through the aperture of the member, the member distal end being proximal of the housing distal end with the needle in the second position and being operable to maintain the needle distal tip within the housing after the needle has moved from the first position to the second position;
   the housing including a radially outwardly directed projection and a support being positioned radially inwardly of the projection and extending proximally thereof, the projection being operable to engage the interior aspect of the catheter hub and radially moveable inwardly sufficiently to disengage therefrom, the projection being held against moving radially inwardly sufficiently to disengage when the needle is in the first position and being free to move radially inwardly sufficiently to disengage coincident with the needle being moved into the second position, the housing defining a passageway portion starting at a distal-most end of the housing and extending proximally along the support, the passageway portion being distal of the needle in the second position, no part of the housing defining the passageway portion being in direct contact with the needle in the first position.

20. The safety catheter device of claim 19, the member proximal end being rotatable relative to the proximal end of the housing.

* * * * *

UNITED STATES PATENT AND TRADEMARK OFFICE
CERTIFICATE OF CORRECTION

Page 1 of 1

PATENT NO.      : 8,647,301 B2
APPLICATION NO. : 13/527248
DATED           : February 11, 2014
INVENTOR(S)     : Dennis M. Bialecki et al.

It is certified that error appears in the above-identified patent and that said Letters Patent is hereby corrected as shown below:

In the Specification

Column 7

Line approximately 5, "angle a" should be -- angle α --

Column 8

Line approximately 58, "FIGS. 2B and 2B" should be -- FIGS. 2B and 2B' --

Column 9

Line approximately 15-16, "hub 220 Annular" should be -- hub 220. Annular --

Signed and Sealed this
Twenty-seventh Day of May, 2014

Michelle K. Lee
*Deputy Director of the United States Patent and Trademark Office*